(12) United States Patent
Gestner et al.

(10) Patent No.: US 10,240,955 B2
(45) Date of Patent: Mar. 26, 2019

(54) SYSTEM, APPARATUS AND METHOD FOR AUTOMATIC PIPE TYPE DETECTION

(71) Applicant: Reliance Worldwide Corporation, Atlanta, GA (US)

(72) Inventors: Brian Gestner, Atlanta, GA (US); Thea Knudsen, Atlanta, GA (US); Francis M. Mess, Smyrna, GA (US); Jeffrey L. Leaders, Mableton, GA (US)

(73) Assignee: Reliance Worldwide Corporation, Atlanta, GA (US)

( * ) Notice: Subject to any disclaimer, the term of this patent is extended or adjusted under 35 U.S.C. 154(b) by 0 days.

(21) Appl. No.: 15/850,825

(22) Filed: Dec. 21, 2017

(65) Prior Publication Data

US 2018/0113013 A1 Apr. 26, 2018

Related U.S. Application Data

(63) Continuation of application No. 15/609,912, filed on May 31, 2017, now Pat. No. 9,851,230, and a
(Continued)

(51) Int. Cl.
*G01H 5/00* (2006.01)
*G01K 11/00* (2006.01)
(Continued)

(52) U.S. Cl.
CPC .............. *G01F 1/66* (2013.01); *G01F 1/662* (2013.01); *G01F 25/0007* (2013.01);
(Continued)

(58) Field of Classification Search
CPC ....... G01F 1/66; G01N 29/44; G01N 29/4472
(Continued)

(56) References Cited

U.S. PATENT DOCUMENTS 6,158,288 A 12/2000 Smith
6,654,697 B1 11/2003 Eryurek et al.
(Continued)

FOREIGN PATENT DOCUMENTS

WO WO-2014/190261 A2 11/2014

OTHER PUBLICATIONS

Examination Report for CA Application No. 2,969,591, dated Apr. 25, 2018, 4 pages.
(Continued)

*Primary Examiner* — Lisa Caputo
*Assistant Examiner* — Roger Hernandez-Prewit
(74) *Attorney, Agent, or Firm* — Foley & Lardner LLP

(57) ABSTRACT

A fluid flow meter can include a sensor capable of transmitting a transmit signal to propagate, at least partially, through a fluid in a pipe and receiving a respective receive signal. The fluid flow meter can include a memory storing computer code instructions and a plurality of pipe type signatures associated with a plurality of pipe types. Each pipe type signature of a respective pipe type of the plurality of pipe types can include one or more characteristics of receive signals associated with that pipe type. The fluid flow meter can also include a processor communicatively coupled to the sensor and to the memory. When executing the computer code instructions, the processor can determine one or more signal features of the receive signal, and identify a pipe type of the pipe based on the one or more signal features of the receive signal and the plurality of pipe type signatures.

20 Claims, 12 Drawing Sheets

Related U.S. Application Data continuation of application No. PCT/US2015/066106, filed on Dec. 16, 2015.

(60) Provisional application No. 62/093,116, filed on Dec. 17, 2014.

(51) Int. Cl.

| | | |
|---|---|---|
| *G01N 9/24* | (2006.01) | |
| *G01N 24/00* | (2006.01) | |
| *G01N 29/02* | (2006.01) | |
| *G01N 29/04* | (2006.01) | |
| *G01S 15/00* | (2006.01) | |
| *G01V 1/28* | (2006.01) | |
| *G01F 1/66* | (2006.01) | |
| *G01N 29/024* | (2006.01) | |
| *G01N 29/44* | (2006.01) | |
| *G01F 25/00* | (2006.01) | |

(52) U.S. Cl.
CPC ........... *G01N 29/024* (2013.01); *G01N 29/44* (2013.01); *G01N 29/4472* (2013.01); *G01F 1/667* (2013.01)

(58) Field of Classification Search
USPC ........................................ 73/597; 702/45, 48
See application file for complete search history.

(56) References Cited

U.S. PATENT DOCUMENTS

| | | |
|---|---|---|
| 6,883,386 B2 | 4/2005 | Osone et al. |
| 7,712,382 B2 | 5/2010 | Takeda et al. |
| 8,117,918 B2 | 2/2012 | Gysling |
| 2002/0134140 A1 | 9/2002 | Baumoel |
| 2009/0229364 A1* | 9/2009 | Gysling ................. G01B 17/02 73/623 |
| 2011/0271769 A1 | 11/2011 | Kippersund et al. |
| 2013/0080081 A1 | 3/2013 | Dugger et al. |
| 2014/0238136 A1* | 8/2014 | Ten Grotenhuis et al. ................. G01N 29/0654 73/592 |

OTHER PUBLICATIONS

Corrected Notice of Allowance for U.S. Appl. No. 15/609,912 dated Oct. 20, 2017.
International Preliminary Report on Patentability for PCT/US2015/066106 dated Jun. 20, 2017 (9 pages), Jun. 29, 2017.
International Search Report PCT/US2015/066106 dated Feb. 10, 2016, 2 pages.
Notice of Allowance on for U.S. Appl. No. 15/609,912 dated Aug. 16, 2017.
Written Opinion PCT/US2015/066106 dated Feb. 10, 2016, 7 pages.
Extended European Search Report for EP Application No. 15870989.9 dated Aug. 10, 2018, 6 pages.

* cited by examiner

SYSTEM, APPARATUS AND METHOD FOR AUTOMATIC PIPE TYPE DETECTION

RELATED APPLICATION

This application is a continuation of and claims priority to U.S. Non-Provisional application Ser. No. 15/609,912, filed May 31, 2017, which claims priority to International Application No. PCT/US2015/066106, filed Dec. 16, 2015, which claims priority to U.S. Provisional Application No. 62/093,116, entitled "SYSTEM, APPARATUS AND METHOD FOR AUTOMATIC PIPE TYPE DETECTION" and filed on Dec. 17, 2014, all of which are incorporated herein by reference in their entirety.

BACKGROUND

Fluid flow meters can allow for fluid flow monitoring in fluid distribution systems. In particular, a fluid flow meter allows for measuring the amount of fluid flowing through a lumen, such as a pipe. For example, water meters are used to measure the amount of water used by a building, home, or apartment. A traditional water meter (or other fluid flow meter) is usually built as a device including a tailpiece that is coupled, through pluming, to pipes in a fluid flow distribution system. Some recent fluid flow meters are built as non-intrusive meters that can be mounted on a pipe. Such fluid flow meters are capable of monitoring, without physically interfering with, fluid flow within the respective pipes.

SUMMARY

According to at least one aspect, a fluid flow meter can include an ultrasonic sensor capable of transmitting a transmit signal to propagate, at least partially, through a fluid in a pipe and receiving a respective receive signal. The fluid flow meter can include a memory storing computer code instructions and a plurality of pipe type signatures associated with a plurality of pipe types. Each pipe type signature of a respective pipe type of the plurality of pipe types can include one or more characteristics of receive signals associated with that pipe type. The fluid flow meter can also include a processor communicatively coupled to the sensor and to the memory. When executing the computer code instructions, the processor can determine one or more signal features of the receive signal, and identify a pipe type of the pipe based on the one or more signal features of the receive signal and the plurality of pipe type signatures.

According to at least one other aspect, a method for identifying a pipe type of a pipe associated with a fluid flow meter can include a sensor of the fluid flow meter transmitting a transmit signal to propagate, at least partially, through a fluid in the pipe, and receiving a receive signal responsive to transmitting the transmit signal. The method can also include a processor determining one or more signal features of the receive signal, and identifying a pipe type of the pipe based on the one or more signal features of the receive signal and a plurality of pipe type signatures associated with a plurality of pipe types. Each pipe type signature of a respective pipe type of the plurality of pipe types can include one or more characteristics of receive signals associated with that pipe type.

According to at least one other aspect, a non-transitory computer-readable medium can include computer code instructions stored thereon. The computer code instructions, when executed by a processor, can cause a sensor of a fluid flow meter to transmit a transmit signal for propagating, at least partially, through a fluid in a pipe and receive a receive signal responsive to transmitting the transmit signal. The computer code instructions also can cause the processor to determine one or more signal features of the receive signal, and identify a pipe type of the pipe based on the one or more signal features of the receive signal and a plurality of pipe type signatures associated with a plurality of pipe types. Each pipe type signature of a respective pipe type of the plurality of pipe types including one or more characteristics of receive signals associated with that pipe type.

DETAILED DESCRIPTION

Figure 1:
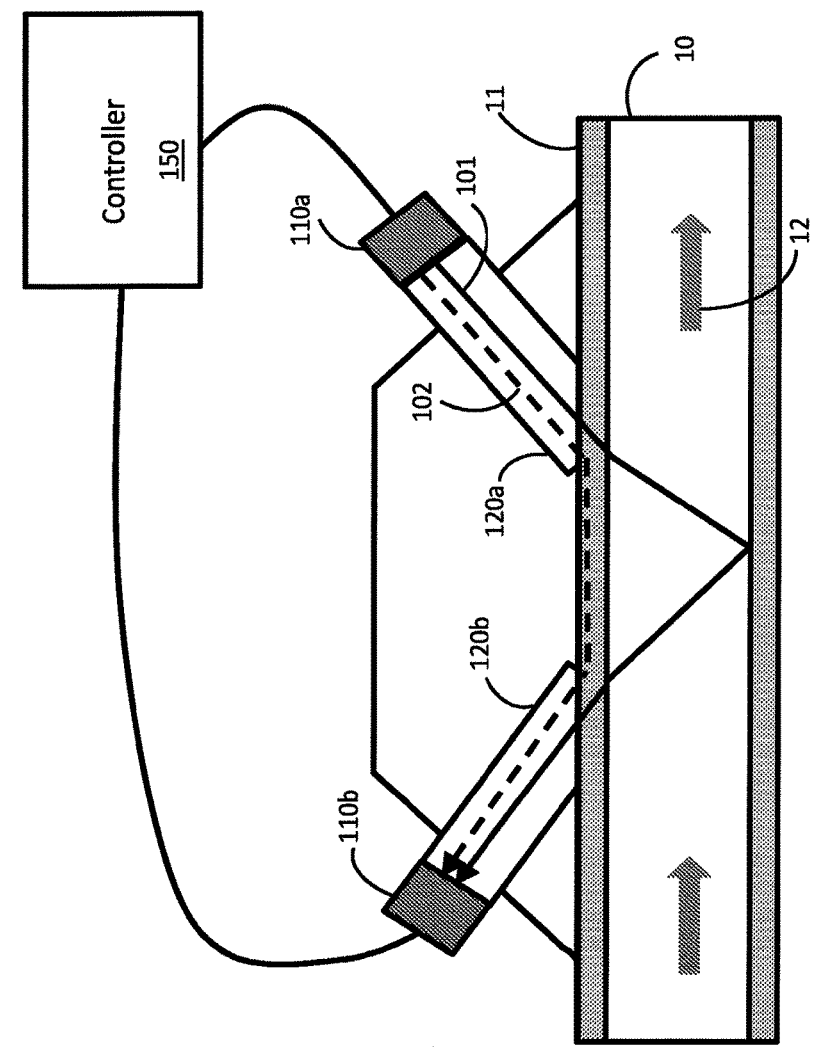
FIG. 1 shows a diagram illustrating a flow rate meter system.

Systems, devices and methods described in the current disclosure allow a fluid flow meter system to detect the type of a pipe on which the system is mounted. A fluid flow meter (such as an ultrasonic fluid flow meter) can measure fluid flow rate or fluid flow velocity of a fluid flowing within a lumen (such as a pipe) by transmitting a signal to propagate through the fluid and measuring (or estimating) the effect of the fluid on a respective measurement signal associated with a received copy (or version) of the transmitted signal. For instance, the fluid flow meter can cause signals to propagate upstream and downstream across the fluid and measure the difference between propagation times for upstream and downstream signals. In the current disclosure, a signal propagating downstream is a signal propagating (while may be bouncing off the interior pipe wall) in the direction of the fluid flow, whereas a signal propagating upstream is a signal propagating (while may be bouncing off the interior pipe wall) in the opposite direction compared to the fluid flow. The propagation time difference can be proportional to the flow rate of the fluid. The fluid flow meter can compute (or estimate) the fluid flow rate (or fluid flow velocity) of the fluid based on measured difference between propagation times for upstream and downstream signals. In some embodiments, the fluid flow meter system can employ difference in propagation times for upstream and zero-flow signals or difference in propagation times for zero-flow and downstream signals to measure (or estimate) the fluid flow rate (or fluid flow velocity) of the fluid. Measuring (or estimating) the difference in propagation times can include determining signal propagation time or signal time of arrival (ToA) based on measurement signals, for example, using signal processing techniques.

The measured (or estimated) signal propagation times (or ToAs) can be affected by many factors such as the type of pipe (e.g., including the size and material of the pipe). Among other things, the type of material of the pipe, the pipe size (e.g., pipe diameter), the pipe wall thickness or a combination thereof can influence characteristics (such as propagation time, energy, shape) of received copies of the propagating signals. For example, the distance traveled by a signal propagating through the fluid in a given pipe can change based on the pipe diameter. Also, for ultrasonic signals, for instance, the material of the pipe can affect reflection and transmission coefficients of the propagating signals within or at the boundary of the pipe wall. For electromagnetic signals, the material of the pipe can affect reflection and refraction coefficients at the boundaries of the pipe wall. As such, substantial errors can be introduced when estimating signal propagation (or ToA) if the pipe type is not properly modeled or taken into account within the signal processing techniques employed to estimate signal propagation times (or ToAs) of received copies of the propagating signals. For instance, some signal processing techniques employed to estimate signal propagation times (or ToAs) of received signals involve signal template matching. In such instances, distinct waveform templates can be used for different types of pipes when measuring (or estimating signal propagation time or ToA). Using coarse signal templates for different types or distinct sizes of pipes can result in matching errors when estimating the signal propagation time or ToA, and therefore lead to errors in measured (or estimated fluid flow rates or fluid flow velocities.

Furthermore, when using ultrasonic transducers, fluid flow rate (or fluid flow velocity) is proportional to the difference between upstream signal propagation time and downstream signal propagation time. The proportionality constant between such difference the fluid flow rate (or fluid flow velocity), however, can be different for each pipe type. As such, correctly identifying a pipe type for a pipe that is being used leads to using the correct proportionality constant and, therefore, results in higher precision when measuring fluid flow rate (or fluid flow velocity). Even in cases (e.g., for some fluids) where the relationship between fluid flow rate (or fluid flow velocity) and the difference between upstream signal propagation time and downstream signal propagation time may not be linear, the nonlinearity may vary based on the pipe type. As such, knowing the pipe type allows to use the proper mapping function (e.g., selecting a lookup table) to determine fluid flow rate (or fluid flow velocity) based on difference in propagation times between upstream and downstream signal. In some implementations, difference in propagation times between upstream and zero-flow signals or zero-flow and downstream signals may be employed in determining fluid flow rate (or fluid flow velocity).

In order to serve flow rate meters for a variety of pipes, one approach may be to design and manufacture distinct flow rate meters for different types of pipes. Such approach is not cost effective. Furthermore, providing pipe-type-specific fluid flow meters may lead to confused consumers and may result in relatively high product return rate. Another approach is to design fluid flow meters that are adjustable by users based on the pipe type used with each fluid flow meter. Such approach can add complexity to the design of such fluid flow meters and can put unnecessary burden on consumers. Many consumers do not necessarily recognize the different types of pipes available to them in the market and may end up not properly adjusting (or calibrating) the fluid flow meters.

In the current disclosure, systems, devices and methods for automatically detecting (or identifying) a pipe type are disclosed. According to at least one aspect, the systems, devices, and methods described in the current disclosure employ pipe-type signatures (or pipe-type signal signatures) to identify a pipe on which a fluid flow meter is attached. A pipe signature can include one or more signal parameter values, one or more signal features, or a combination thereof that characterize measurement signals associated with a specific pipe type. In some embodiments, the signal parameter value(s) or the signal feature(s) can be determined based on a distinction between a first signal portion of a measurement signal associated with a propagation path confined to the pipe wall and a second signal portion associated with a propagation path mainly through the fluid flowing within the pipe. The systems, devices and methods described in the current disclosure can use relative characteristics (such as, relative energy or relative time delay) of the two signal portions of the measurement signal to automatically detect (or identify) the pipe type.

FIG. 1 shows a diagram illustrating a fluid flow meter system 100 mounted on a pipe 10 (or a lumen in general). The fluid flow meter system 100 includes two ultrasonic transducers 110a and 110b (also referred to either individually or collectively as transducer(s) 110) and a controller 150 coupled to the ultrasonic transducers 110. Each transducer 110 can be associated with a respective waveguide 120a and 120b. In some implementations, the waveguides 120 can be optional. That is, the transducers 110 can be mounted directly to the pipe 10 without waveguides 120. As shown in FIG. 1, the ultrasonic transducers 110 can be mounted in a non-invasive manner (such that the ultrasonic transducers 110 or the waveguides 120 do not physically interfere with the fluid flow within the pipe 10). The arrows 12 indicate the fluid flow direction within the pipe 10.

The controller 150 can cause a first ultrasonic transducer (such as transducer 110a) to transmit an ultrasonic signal and cause the second ultrasonic transducer (such as transducer 110b) to receive a copy (or a version) of the transmitted signal. The controller 150 can process measurement signals corresponding to respective transmitted signals to detect a pipe type or estimate a signal ToA, signal propagation time, and/or fluid flow rate (or fluid flow velocity). The controller 150 can include one or more of a microprocessor, microcontroller, digital signal processor (DSP), and application-specific integrated circuit (ASIC). The controller 150 can include an analog-to-digital converter (ADC) for sampling received copies of transmitted signals and generating respective measurements signals. The controller 150 can include a memory to store measurement signal samples or parameters thereof, and computer code instructions executable by a processor of the controller 150. The computer code instructions when executed by the controller 150 can perform any of the methods described in this disclosure. The computer code instructions can be stored in a non-transitory computer-readable medium. The controller 150 can perform other processes for monitoring the ultrasonic transducers 110, managing power consumption of the system 100, processing data, communicating with other electronic (or electromechanical) devices, or a combination thereof. The fluid flow meter system 100 can also include a communication interface, such as a wireless communication interface, a Wi-Fi communication interface, a wired communication interface, etc., for communicating with external devices. For example, the fluid flow meter system 100 can communicate with a mobile device (such as a smartphone, a tablet, laptop, etc.) or a computing device (such as a desktop, a cloud server, etc.) via one or more communication networks.

In some implementations, the system 100 can include more than two ultrasonic transducers 110. In some implementations, each ultrasonic transducer 110 in the system 100 can be capable of acting as a transmitter and a receiver. In some implementations, some ultrasonic transducers 110 in the system 100 can be configured to act as transmitters while others can be configured to act as receivers. While the system 100 employs the ultrasonic transducers 110 to transmit or receive signals, other types of signal transmitters, receivers, or transducers, such as acoustic or electromagnetic transmitters, receivers or transducers can be employed.

A signal transmitted by a transmitting ultrasonic transducer (such as transducer 110a) can propagate through more than a single propagation path to reach the receiving ultrasonic transducer (such as transducer 110b). In FIG. 1, a first portion of the transmitted signal (referred to hereinafter as the fluid signal 101) can propagate through the waveguide 120a associated with the transmitting ultrasonic transducer 110a and cross the pipe wall 11 to continue propagating through the fluid flowing in the pipe 10. Depending on the way the transducers 110 are arranged with respect to one another and with respect to the pipe 10, the fluid signal 101 can bounce back off the interior surface of the pipe wall 11 and propagate towards the waveguide 120b to reach the receiving ultrasonic transducer (such as transducer 110b). The fluid signal 101 can cross through the pipe wall 11 to reach the fluid in the pipe 10, and cross through the pipe wall again when leaving the fluid towards the waveguide 120b. The waveguides 120a and 120b can be optional, in which case, the fluid signal 101 can propagate from/towards the transducer 110 towards/from the pipe wall 11. In some implementations, the fluid signal can propagate through an air gap or some material located between the fluid flow meter system 100 and the pipe wall 11.

A second portion of the transmitted signal (referred to hereinafter as the pipe signal 102) can propagate through the waveguide 120a associated with the transmitting ultrasonic transducer 110a then through (or on) the pipe wall 11 until it reaches the waveguide 120b (or the receiving transducer 110b if there is no waveguide 120b) where it propagates towards the receiving ultrasonic transducer 110b. Given the different lengths and the different materials associated with the different propagation paths of the fluid signal 101 and the pipe signal 102, respective received versions of these signals and corresponding measurement signals (e.g., sampled versions of received signals) can have substantially different characteristics.

Figure 2:
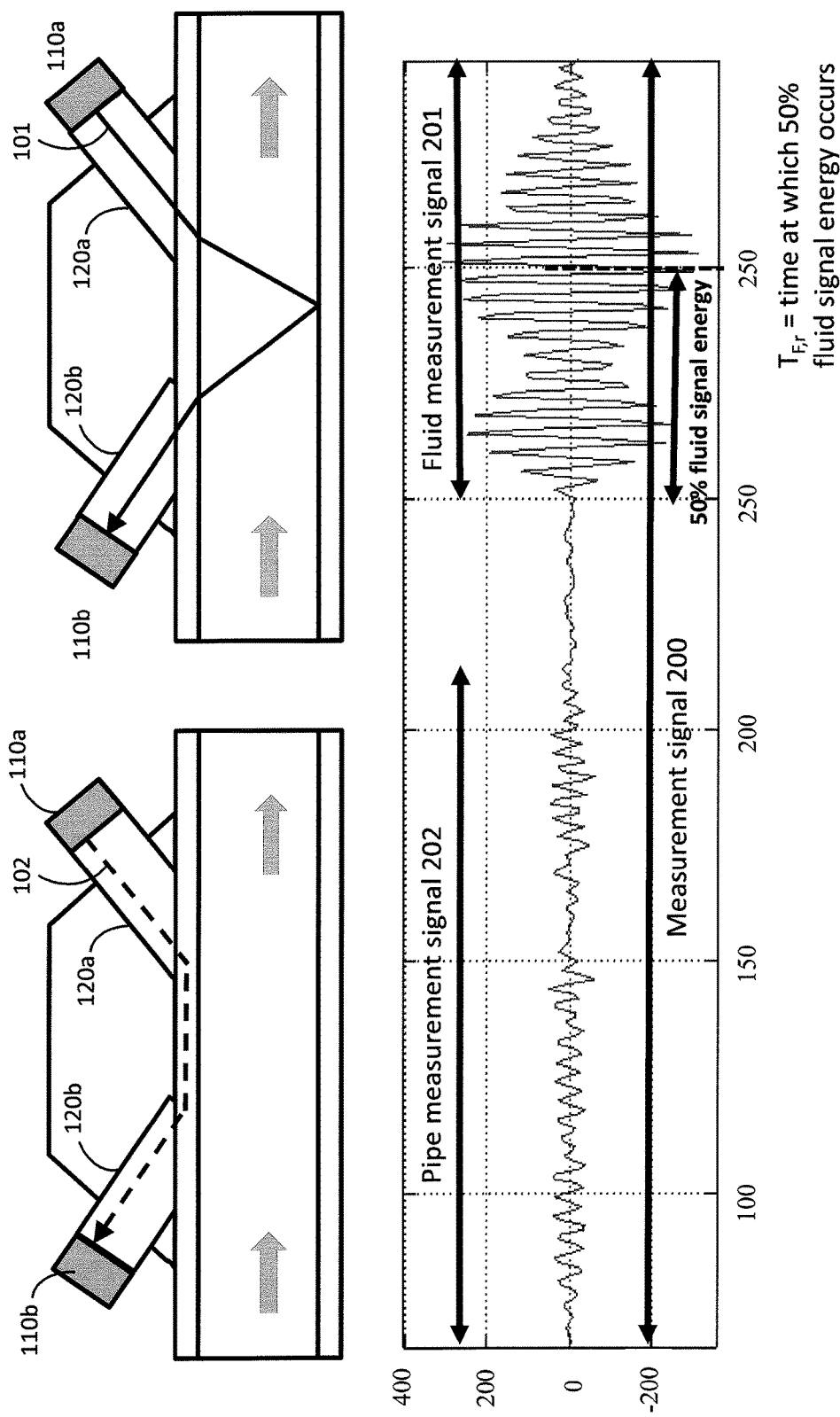
FIG. 2 shows a plot illustrating a received ultrasonic signal 200 depicting signal portions associated with distinct propagation paths.

FIG. 2 shows a plot illustrating a measurement signal 200 including signal portions associated with distinct propagation paths. The measurement (or received) signal 200 can be viewed as a summation of the pipe measurement signal 202 and the fluid measurement signal 201. The pipe measurement signal 202 corresponds to (or represents a received version of) the pipe signal 102, and the fluid measurement signal 201 corresponds to (or represents a received version of) the fluid signal 101. The pipe measurement signal 202 starts at the time instance $t_{p,s}$ and ends at the time instance $t_{p,e}$. The fluid measurement signal 101 starts at the time instance $t_{p,s}$ and ends at the time instance $t_{f,e}$. Given the difference in ToAs $t_{p,s}$ and $t_{f,s}$, the pipe measurement signal 202 and the fluid measurement signal 201 are non-overlapping. Furthermore, the energy of the fluid measurement signal 201 can be substantially higher than that of the pipe measurement signal 202. In addition, the shapes of the pipe measurement signal 202 and the fluid measurement signal 201 can be substantially different from each other.

Given that both the fluid measurement signal 201 and the pipe measurement signal 202 are associated with the same transmit signal originating at the transmitting ultrasonic transceiver 110a, the differences between the signal features (such as ToA, shape, and energy) of the fluid measurement signal 201 and the pipe measurement signal 202 reflect the difference between the respective propagation paths and propagation media through which each of the fluid signal 101 and the pipe signal 102 propagates between the two ultrasonic transceivers 110. For instance, given that the propagation path of the fluid signal 101 is longer than that of the pipe signal 102, the ToA of the fluid signal 101 may be delayed with respect to that of the pipe signal 102. Furthermore, as the diameter of the pipe 10 increases so does the difference between the ToAs of both signals. Also, the intrinsic elastic properties (such as propagation speed) of the pipe wall 11 and those of the fluid flowing within the pipe 10 can affect signal features (such as ToAs, signal shape, signal energy, etc.) of each of the fluid measurement signal 201 and the pipe measurement signal 202 differently. In addition, the difference between the propagation dynamics of the pipe wall 11 and those of the fluid flowing within the pipe 10 can result in differences between the shape and energy of the pipe measurement signal 202 and those of the fluid measurement signal 201. Accordingly, features or characteristics of the fluid and pipe measurement signals 201 and 202, such as the signal propagation time (or ToA), signal shape or signal energy, can be indicative of the characteristics of the pipe 10, such as the geometry (e.g., diameter) or material. In particular, distinct pipes can have different effects on fluid measurement signal 201 and the pipe measurement signal 202. As such, signal features or parameters associated with both the fluid measurement signal 201 and the pipe measurement signal 202 can be used to distinguish between distinct pipes or to identify a pipe 10 based on one or more respective measurement signals 200.

Given the received signal 200, the controller 150 can, for example, determine one or more relative characteristic parameters of the fluid measurement signal 201 with respect to corresponding characteristics of the measurement signal 200 or the pipe measurement signal 202. In some implementations, the controller 150 can determine one or more relative characteristic parameter(s) of the pipe measurement signal 202 with respect to corresponding characteristics of the measurement signal 200 or the fluid measurement signal 101. The controller 150 can use the determined relative characteristic parameter(s) to determine a pipe type, for instance, among a plurality of pipe types. The controller 150 can determine the duration of the received signal 200 to be used based on experimental data obtained for different types of pipes. In some implementations, the controller 150 can automatically determine the start time of the measurement signal 200 (or ToA), for instance, with respect to the time at which the transmitting ultrasonic transducer 110 starts the transmission of the transmit signal, based on detected increase in signal energy (e.g., compared to a threshold). In some implementations, the controller 150 can determine the start time of the measurement signal 200 (or ToA) based on predefined values stored in the controller 150. Such predefined values can be obtained through experimental data collected using a variety of pipes with distinct types.

One of the relative characteristic parameters determined by the controller 150 can be indicative of the relative energy of the fluid measurement signal 201 or the pipe measurement signal 202. In some implementations, an ADC associated with the controller 150 can sample a received signal to obtain the measurement signal 200, for example, having N samples (e.g., x[0], . . . , x[N−1]). The controller 150 can compute the total received signal energy of the measurement signal 200 as $E = \Sigma_0^{N-1}|x[n]|$. The controller 150 can also compute energy of the fluid measurement signal 201 and the energy of the pipe measurement signal 202 as $E_F = \Sigma_{k_{f,s}}^{k_{f,e}}|x[n]|$ and $E_P = \rho_{k_{p,s}}^{k_{p,e}}|x[n]|$, respectively. The integer values $k_{f,s}$ and $k_{f,e}$ represent the indices of the first and last samples of the fluid measurement signal 201, respectively. The integer values $k_{p,s}$ and $k_{p,e}$ represent the indices of the first and last samples of the pipe measurement signal 202, respectively. In some implementations, the controller 150 can compute the signal energies $E$, $E_F$ and $E_P$ using the squares of the respective signal samples (i.e. $\Sigma|x[n]|^2$). Using the computed energies $E$, $E_F$ and $E_P$, the controller 150 can compute one or more relative energy values as ratios of different energy signals. For example, the controller 150 can compute the relative pipe signal energy parameter $$R = \frac{E_P}{E}$$

indicative of the relative energy of the pipe measurement signal 202. In some implementations, the controller 150 can compute the relative energy parameter as $$R = \frac{E_P}{E}$$

(e.g., compared to the energy of the measurement signal 200) or as $$R = \frac{E_P}{E_F}$$

(e.g., compared to the energy of the fluid measurement signal 201). In some implementations, the controller 150 can compute the relative fluid signal energy $$\left(\text{e.g., as } \frac{E_F}{E} \text{ or as } \frac{E_F}{E_P}\right).$$

The relative fluid signal energy of the fluid measurement signal 201 or the relative pipe signal energy of the pipe measurement signal 202 can be computed using other mathematical formulations.

The relative energy parameter R can reflect the relative signal energy of the fluid measurement signal 201 and/or the pipe measurement signal 102 compared to each other or compared to the total energy of the measurement signal 200. As such, the relative energy parameter R can vary as the diameter of the pipe 10 varies or as the material forming the pipe wall 11 changes. For instance, as the diameter of the pipe 10 increases, the propagation path of the fluid signal 101 becomes longer and the fluid signal 101 can undergo higher attenuation resulting in smaller fluid signal energy. Also, the amount of signal attenuation experienced by the pipe signal 102 depends on the material forming the pipe wall 11. As such, the relative energy parameter R can vary in terms of the pipe type. Accordingly, the controller 150 can employ the relative energy parameter R to detect the pipe type associated with the measurement signal 200.

In some implementations, the controller 150 can use the energy parameters $E_F$, $E_P$, $E$ or a combination thereof, instead of the relative energy parameter(s) R, to determine a pipe type. When using the actual energy parameters, such as $E_F$, $E_P$ or $E$, to determine a pipe type, the controller 150 can take into account the amplitude(s) of the respective transmitted signal(s), the gain associated with the receiving transducer 110b, or a combination thereof. In other words, the process of using the actual energy parameters to determine a pipe type can depend on the amplitude(s) of the transmitted signal(s) or the gain associated with the receiving transducer 110b. For instance, if such process involves comparing energy values to respective thresholds, the threshold values used can depend on amplitude(s) of the transmitted signal(s) or the gain associated with the receiving transducer 110b.

Among signal parameters or signal features that can be used to identify a pipe type, the controller 150 can determine a time value $T_{F,r}$ indicative of a time instance at which a specific portion (e.g., equal to a ratio or percentage r) of the fluid signal energy $E_F$ is received (or occurs) at the receiving transducer 110b. In other words, the time instance is defined such that the energy of the part of the signal between the start of the fluid measurement signal 201 and the time instance $T_{F,r}$ is equal to fraction r of the fluid signal energy $E_F$. In some implementations, the value r can be 10%, 20%, 40%, 50%, 70%, or any other percentage value or fraction or decimal value between 0 and 1. In some implementations, the controller 150 can determine the time value $T_{F,r}$ as $T_{F,r} = \mathrm{argmin}_{k_{f,s} \le m \le k_{f,e}} |r \times E_F - \Sigma_{k_{f,s}}^m |x[n]||$ or as $T_{F,r} = \mathrm{argmin}_{k_{f,s} \le m \le k_{f,e}} |r \times E_F - \Sigma_{k_{f,s}}^m |x[n]|^2|$. Since the signal propagation characteristics (such as the propagation speed and the signal attenuation) depend on the propagation path and the propagation media through which the ultrasonic signal propagates, the time value $T_{F,r}$ varies with the geometry (e.g., diameter) of the pipe 10 and the material forming the pipe wall 11. In other words, the time parameter $T_{F,r}$ can vary in terms of the pipe type. Accordingly, the controller 150 can employ the time parameter $T_{F,r}$ to detect the pipe type associated with the measurement signal 200.

In some implementations, the controller 150 can determine a time parameter $T_{P,r}$ indicative of a time instance at which a specific portion (e.g., equal to fraction or percentage value r) of the pipe signal energy $E_P$ is received (or occurs) at the receiving transducer 110b. The controller 150 can use the time parameter $T_{P,r}$ instead of, or in combination with, the time parameter $T_{F,r}$ to determine the pipe type. In some implementations, the time parameter(s) $T_{F,r}$ or $T_{P,r}$ can be defined as the time instance(s) at which the amplitude(s) of the received fluid and pipe measurement signals 201 and 202 exceed respective threshold value(s).

Figure 3:
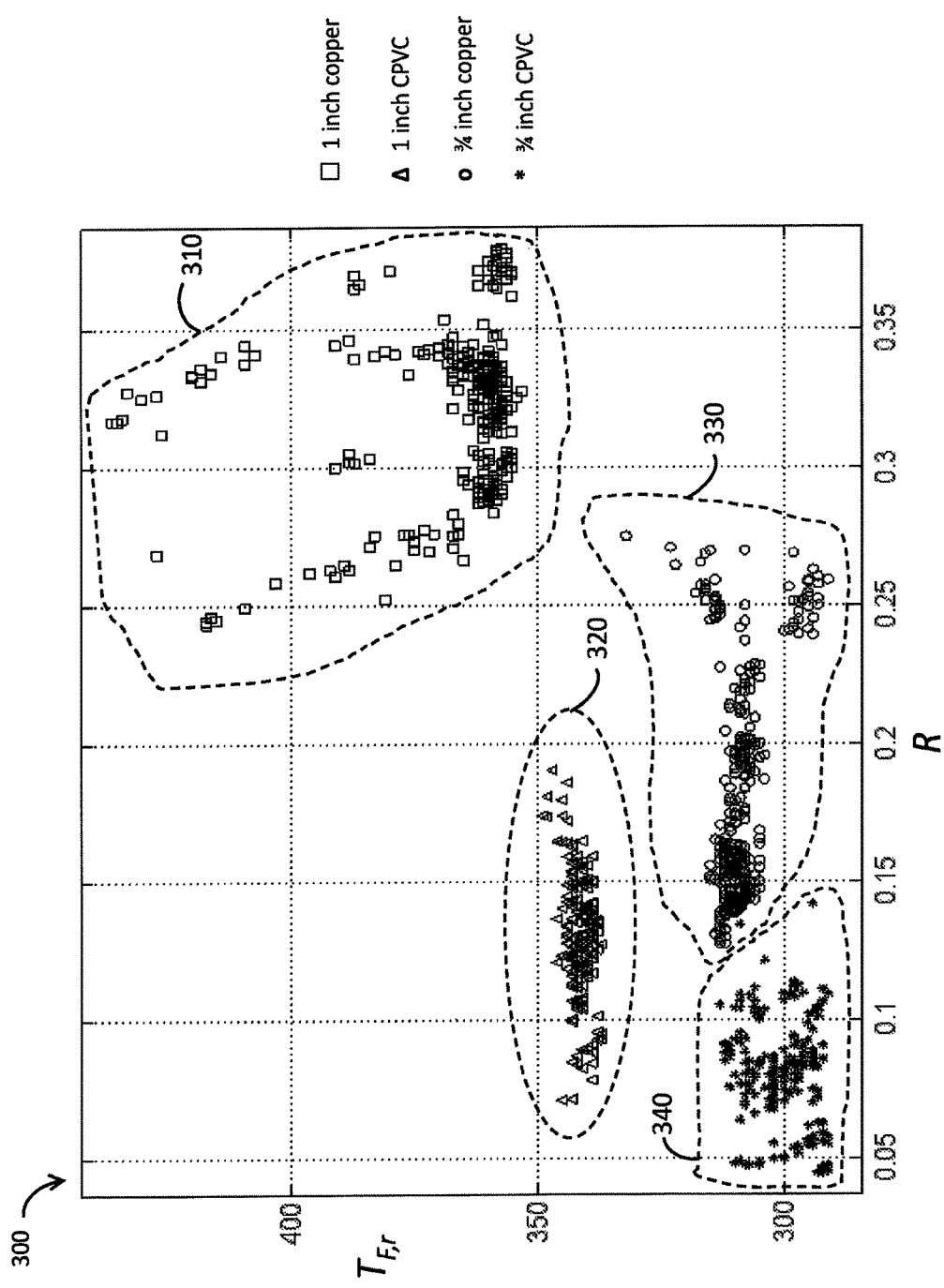
FIG. 3 shows a graph illustrating experimental data obtained for four different pipes.

FIG. 3 shows a graph 300 illustrating experimental data obtained for four different pipes. The four pipes include a one-inch copper pipe, a one-inch chlorinated polyvinyl chloride (CPVC) pipe, a 0.75-inch copper pipe and a 0.75-inch CPVC pipe. The experimental data includes approximately 100,000 data points (not all are shown in FIG. 3) corresponding to 100,000 experiments. In each experiment, a respective received signal is sampled to generate a corresponding measurement signal, such as the measurement signal 200. For each measurement signal, the corresponding relative energy parameter R and the time value parameter $T_{F,r}$ are computed as $$R = \frac{E_P}{E} \text{ and } T_{F,r} = \operatorname{argmin}_{k_{f,s} \leq m \leq k_{f,e}} \left| 0.5 \times E_F - \sum_{k_{f,s}}^{m} |x[n]| \right|,$$

respectively. The value of r associated with $T_{F,r}$ is 0.5 (or 50%). Each data point in the graph is indicative of the computed relative energy R (x-axis in the graph) and the time value $T_{F,r}$ (y-axis in the graph) associated with a respective experiment. The data points shown in the graph 300 depict four clusters 310, 320, 330 and 340, each of which is associated with a respective pipe of the four pipes. The cluster 310 represents the data points associated with the one-inch copper, the cluster 320 represents the data points associated with one-inch CPVC pipe, the cluster 330 represents the data points associated mainly with the 0.75-inch copper pipe, and the cluster 340 represents the data points associated mainly with the 0.75-inch CPVC pipe.

The clustering shown in FIG. 3 indicates that the relative energy and time value parameters R and $T_{F,r}$ associated with the plurality of experiments reflect the difference in pipe type associated with the illustrated data points. However, while the experimental data shows some data clustering, the clusters 310, 320, 330 and 340 shown in FIG. 3 may not allow for reliable distinction between the different pipes (or pipe types), for instance, through data classification. For example, the clusters 330 and 340 are very close to each other, which would make distinction between 0.75-inch copper pipes and 0.75-inch CPVC pipes based on the R and $T_{F,r}$ parameters difficult and result in a relatively high detection (or identification) error rate. Furthermore, the cluster 330 includes some data points associated with the cluster 340. Overall, the clusters 310, 320, 330 and 340 are not separated apart from each other enough to allow for constructing a reliable classifier.

Figure 4A:
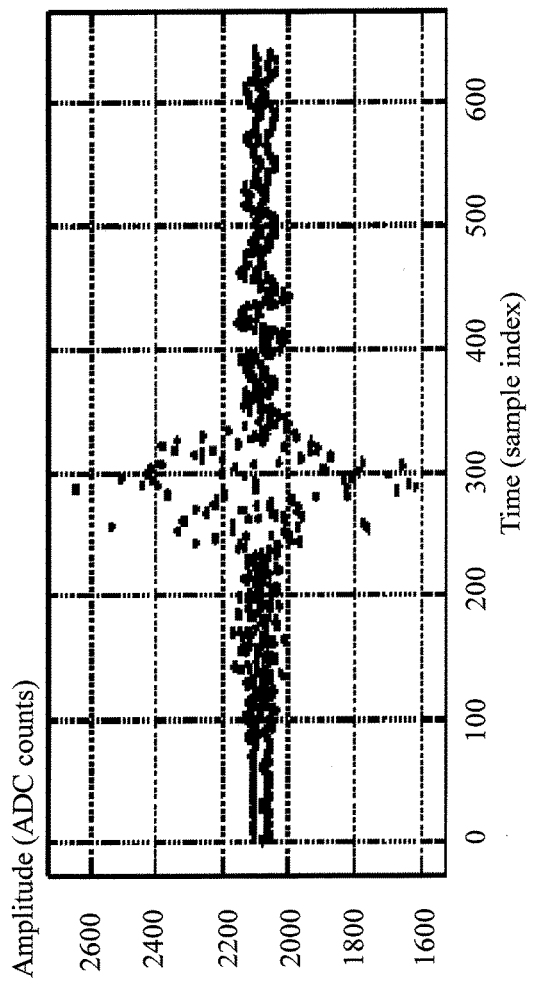
FIGS. 4A and 4B show two plots illustrating signal samples and corresponding frequency spectrum, respectively, of a received signal associated with a 0.75-inch chlorinated polyvinyl chloride (CPVC) pipe.
Figure 4B:
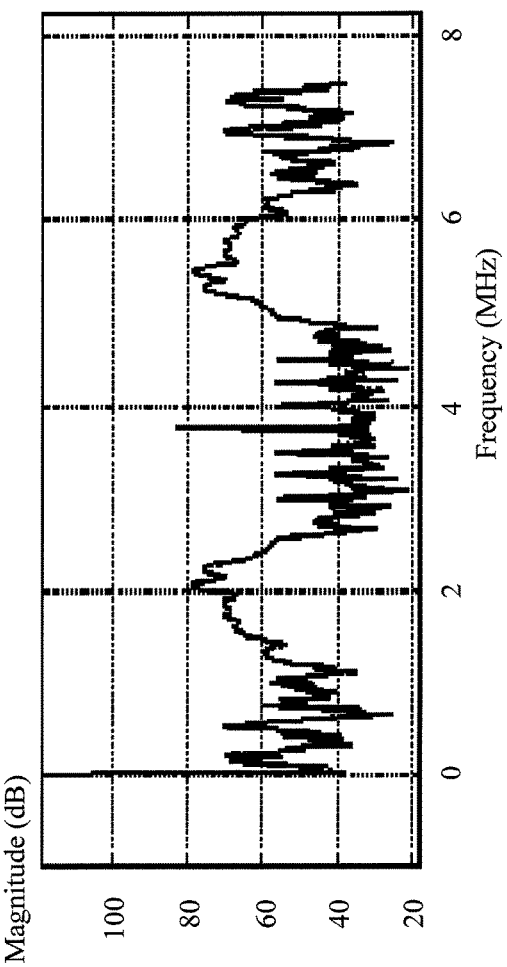

FIGS. 4A and 4B show two plots illustrating, respectively, the signal samples and the frequency spectrum of a measurement signal associated with the 0.75-inch CPVC pipe. The two plots clearly show that the measurement signal suffers from sampling artifacts. Such artifacts can be eliminated, or at least significantly mitigated, by employing a band-pass filter defined based on the spectrum of the transmit signal or the resonance frequency of the transducers. For instance, considering the measurement signal shown in FIG. 4B, a band-pass filter centered at about 2 MHz can be used. Using such band-pass filter can eliminate (or reduce) signal components outside the pass band of the filter.

Figure 5:
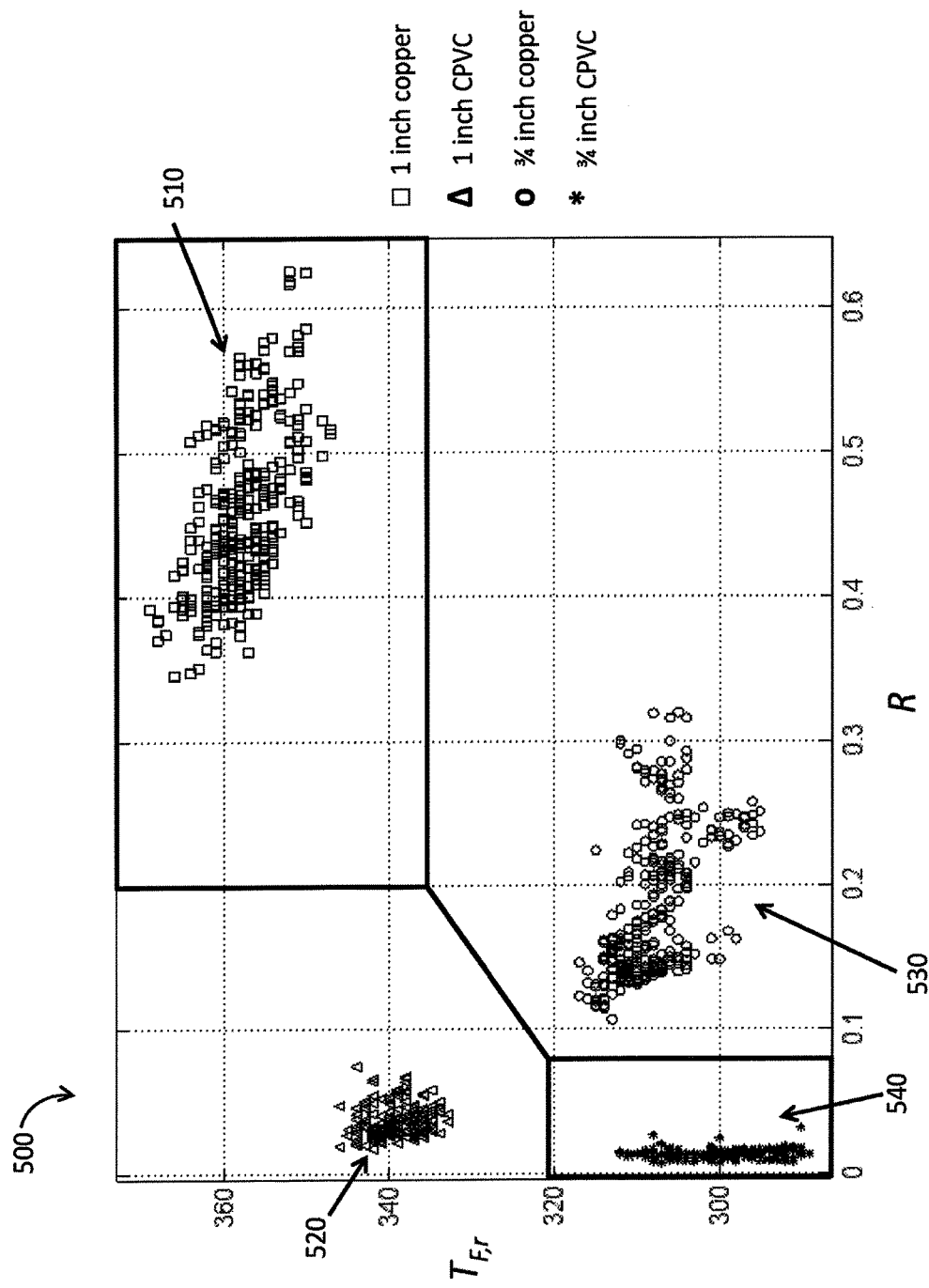
FIG. 5 shows a graph illustrating experimental data obtained for the four different pipes using a band-pass filter.

FIG. 5 shows a graph 500 illustrating experimental data obtained for the four different pipes using a band-pass filter. In other words, received signals (received by receiving transducer(s)) are band-pass filtered upon sampling to generate respective measurement signals. The cluster 510 represents the data points associated with the one-inch copper pipe, the cluster 520 represents the data points associated with one-inch CPVC pipe, the cluster 530 represents the data points associated with the 0.75-inch copper pipe, and the cluster 540 represents the data points associated with the 0.75-inch CPVC pipe. Compared to the experimental data 300 shown in FIG. 3, the experimental data 500 depicts separated clusters that allow for reliable classification of the data points based on the respective pipe type.

Examining the results shown in graph 300 and those shown in graph 500 (as shown in FIGS. 3 and 5, respectively), one can see that $T_{F,r}$ increases as the pipe diameter increases. For example, the clusters 510 and 520, representing experimental data for one-inch pipes, are associated with higher $T_{F,r}$ values than those associated with the clusters 530 and 540, which represent experimental data for 0.75 inch pipes. As the pipe diameter increases, time delay (or propagation time) associated with the fluid signal 101 increase, and so does increase the parameter $T_{F,r}$. Also, plots in FIGS. 3 and 5 show that the value of R associated with a copper pipe is larger than the value of R associated with a CPVC pipe of the same diameter as the copper pipe. For example, R values associated with the cluster 510 are larger than the R values associated with the cluster 520. Also, R values associated with the cluster 530 are larger than the R values associated with the cluster 540.

Figure 6:
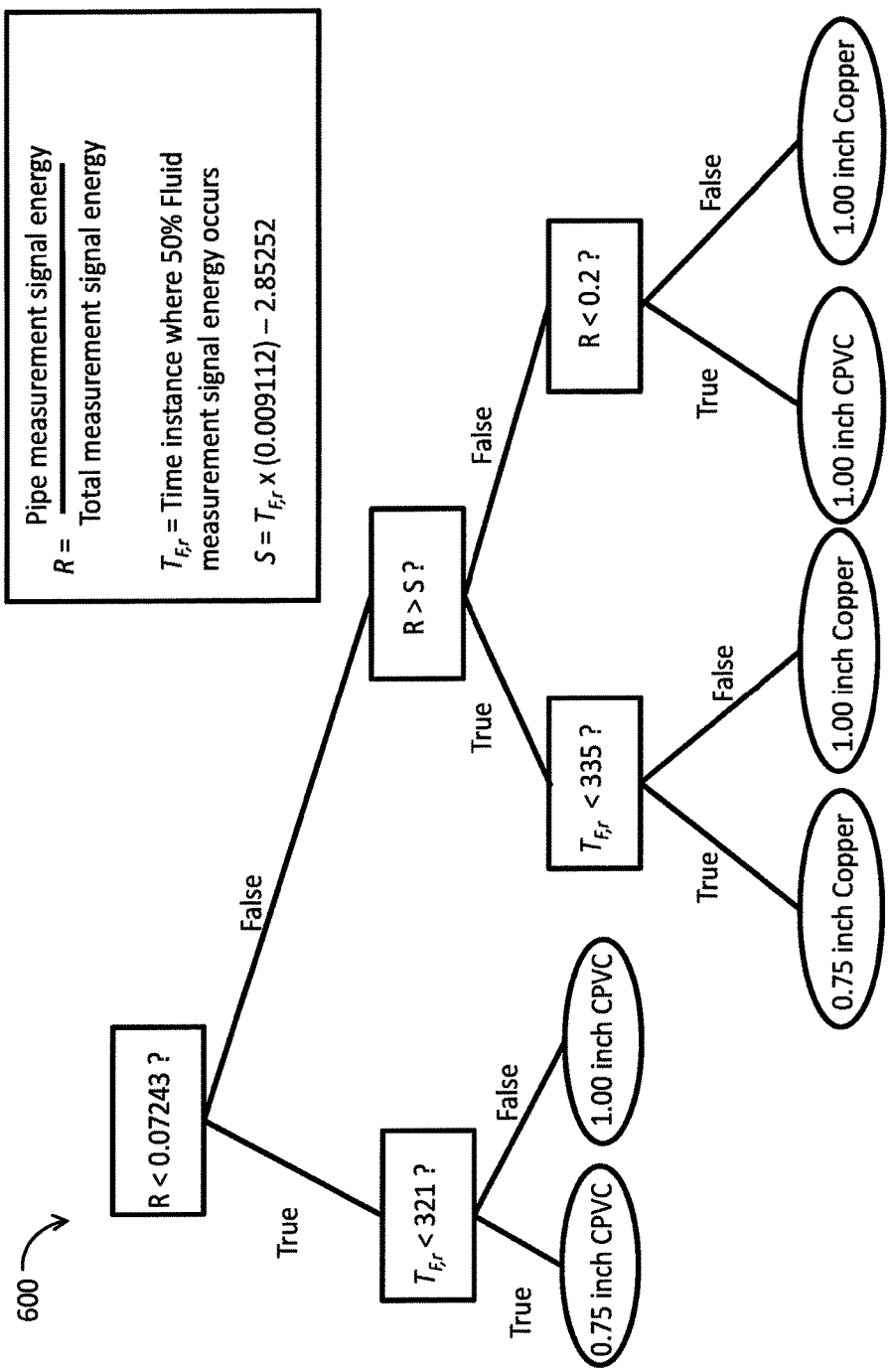
FIG. 6 shows a flow diagram illustrating a classification process based on the data clustering shown in FIG. 5.

FIG. 6 shows a flow diagram illustrating a classification process 600 based on the data clustering shown in FIG. 5. In the flow diagram, the relative energy values R=0.07243 and R=0.2 represent the vertical line separation between the clusters 530 and 540, and the vertical line separation between the clusters 510 and 520, respectively. The time values $T_{F,r}$=321 and $T_{F,r}$=335 represent the horizontal line separation between the clusters 520 and 540, and the horizontal line separation between the clusters 510 and 530, respectively. Each point on the oblique line separating the clusters 520 and 530 satisfies R=S, where as defined in FIG. 6 represents the linear equation defining the oblique line separating the clusters 520 and 530. The flow diagram can be described in many other ways, for instance, based on the order in which the comparisons of R and $T_{F,r}$ values to the values representing separations between different clusters are executed. The controller 150 can detect a pipe type associated with a respective measurement signal 200 by implementing a classification process such as the classification process 600. In other words, using one or more measurements signals 200 generated based on respective receive signals received by the transducer(s) 210, the controller 150 can compute the values of R and $T_{F,r}$ for each measurement signal 200. The controller 150 can apply the classification process 600 for each (R, $T_{F,r}$) pair associated with a respective measurement signal. For each (R, $T_{F,r}$) pair, the respective result of the classification process 600 provides an identification of the type of the pipe on which the fluid flow meter system 100 is mounted. In the case where multiple (R, $T_{F,r}$) pairs (or generally multiple data points) are used, the controller 150 can use the most recurring pipe type in the results provided by the classification process 600 as the identified pipe type of the pipe on which the fluid flow meter 100 is mounted.

Figure 7A:
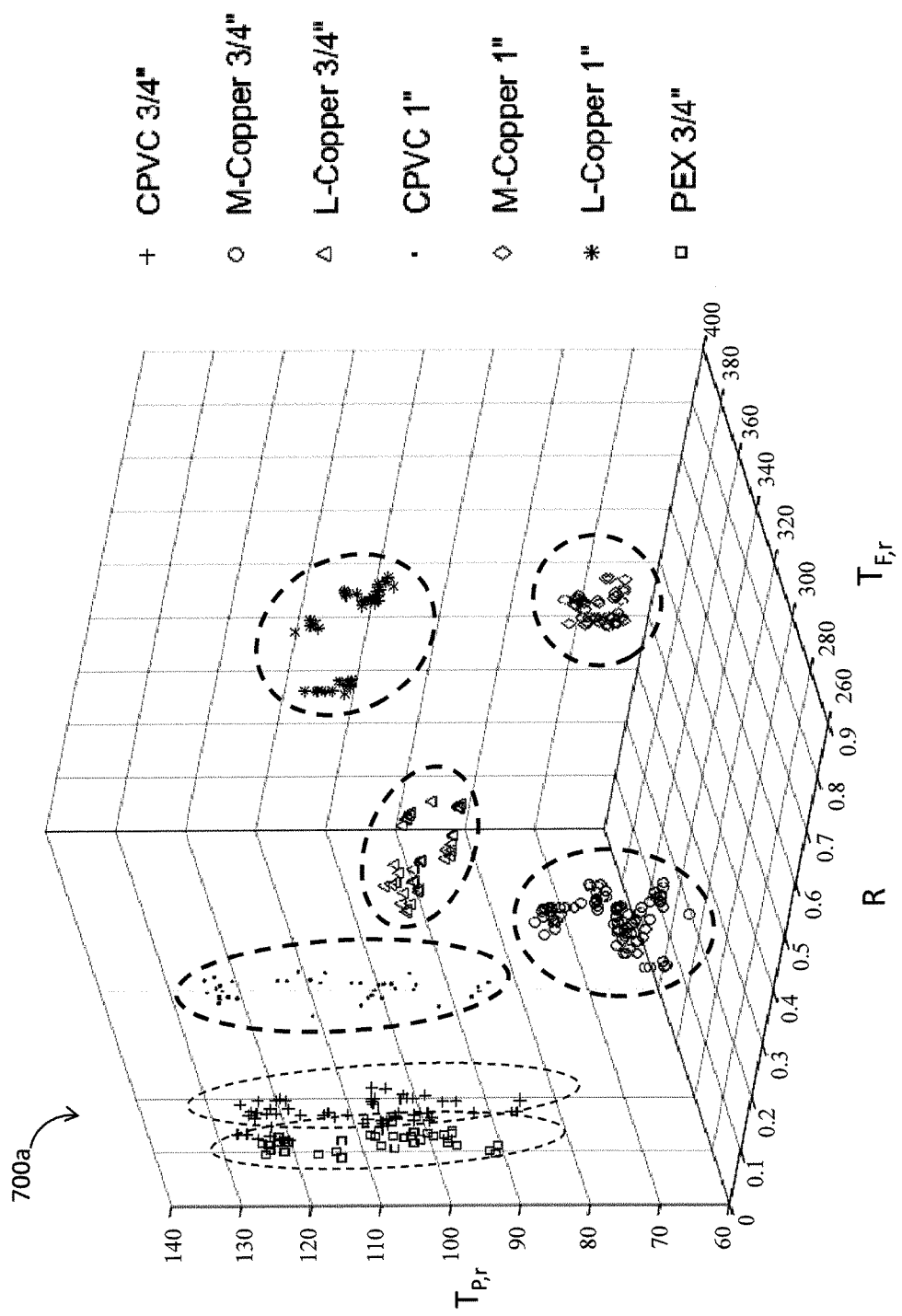
FIG. 7A shows a three-dimensional (3D) graph illustrating experimental data associated with seven pipes of different types.

FIG. 7A shows a three-dimensional (3D) graph 700a illustrating experimental data associated with seven pipes of different types. The seven pipes include a one-inch L-copper pipe, a one-inch M-copper pipe, a one-inch CPVC pipe, a 0.75-inch L-copper pipe, a 0.75-inch M-copper pipe, a 0.75-inch CPVC pipe, and a 0.75-inch crosslinked polyethylene (PEX) pipe. The experimental data is generated using, for each pipe, a plurality of measurement signals 200. For each measurement signal 200, three different parameters, namely R, $T_{F,r}$ and $T_{p,r}$ are computed. The time parameter $T_{p,r}$ can be computed as $T_{P,r} = \operatorname{argmin}_{k_{p,s} \leq m \leq k_{f,e}} |r \times E_P - \Sigma_{k_{p,s}}^{m} |x[n]||$ or as $T_{P,r} = \operatorname{argmin}_{k_{p,s} \leq m \leq k_{p,e}} |r \times E_P - \Sigma_{k_{p,s}}^{m} |x[n]|^2|$. In the graph 700a, the time parameter $T_{p,r}$ represents the time instance at which 50% of the energy of the pipe measurement signal 202 occurs (r=0.5). The parameters R and $T_{F,r}$ are defined similarly as in FIGS. 3 and 5. The 3D graph shows a separate cluster of data points for each of the seven pipes (or pipe types). Apart from the clusters for the 0.75-inch CPVC pipe and the 0.75-inch PEX pipe, which are relatively close to each other, the other clusters are well separated from each other. In particular, the 3D graph 700A shows significant separation between clusters associated with M-copper pipes and L-copper pipes, therefore, indicating that the use of the parameters R, $T_{F,r}$ and $T_{p,r}$ can allow for reliable classification of (and distinction among) the seven pipe types.

Figure 7B:
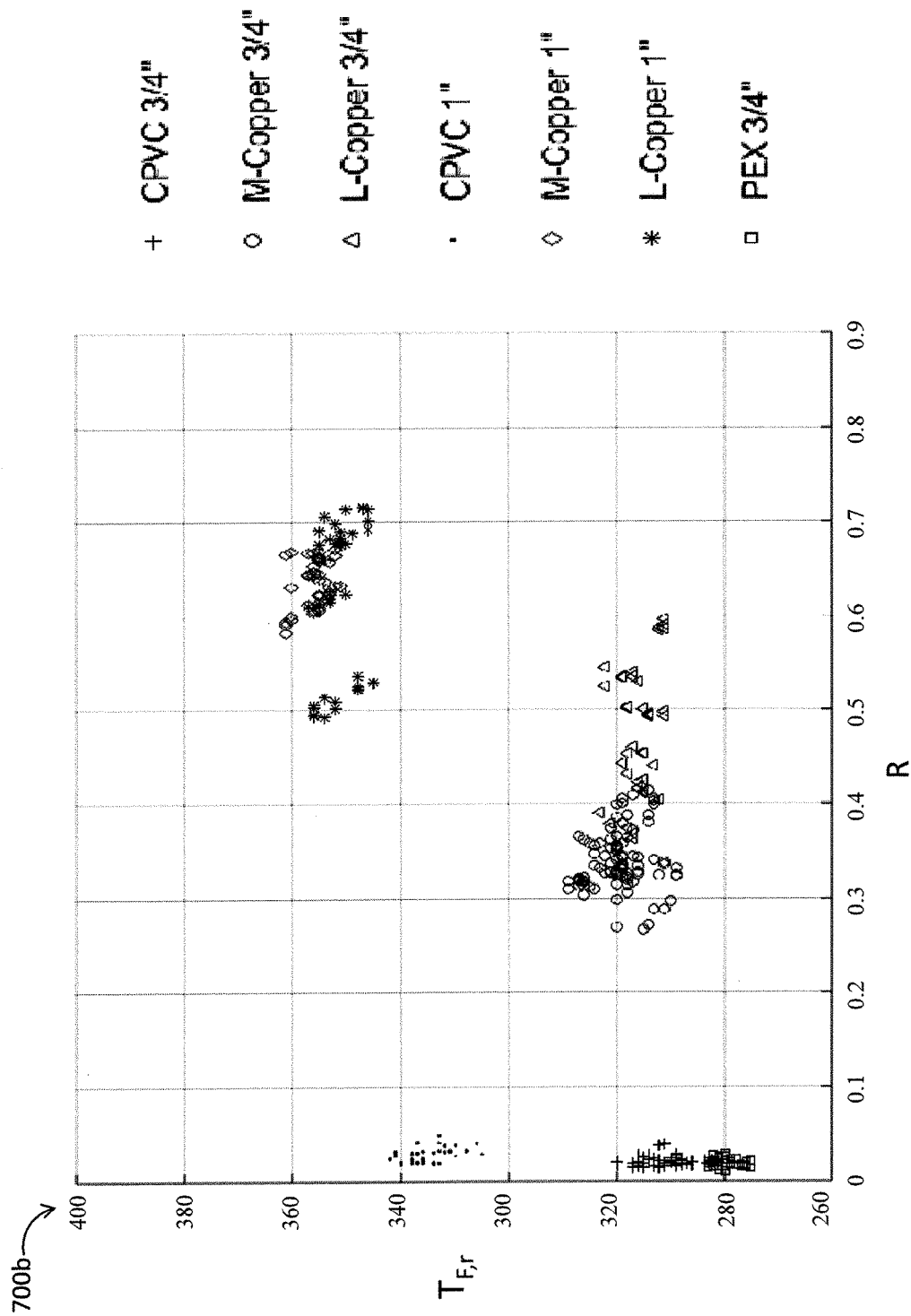
FIGS. 7B-7D show 2D projections of the 3D graph in FIG. 7A.
Figure 7C:
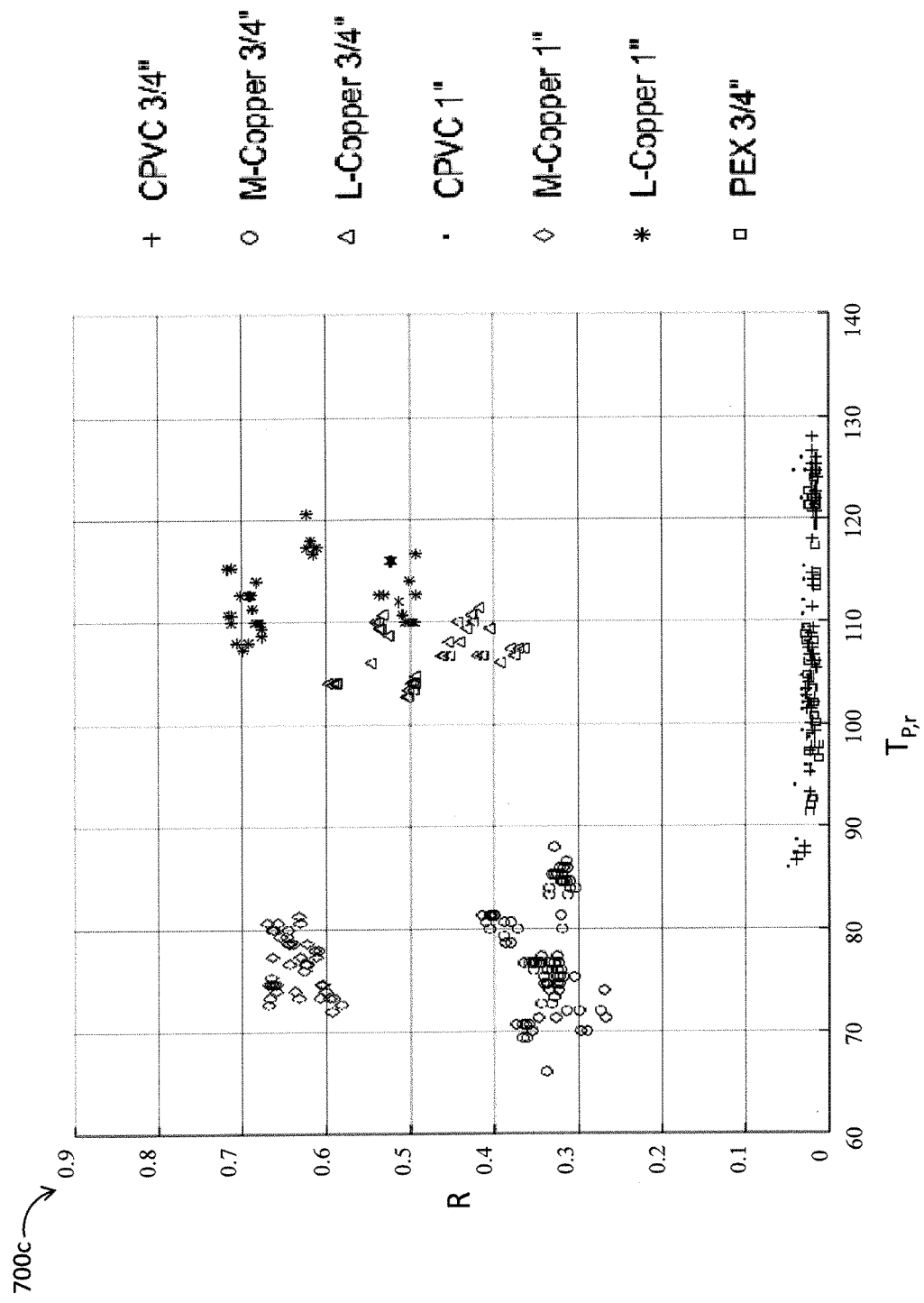
Figure 7D:
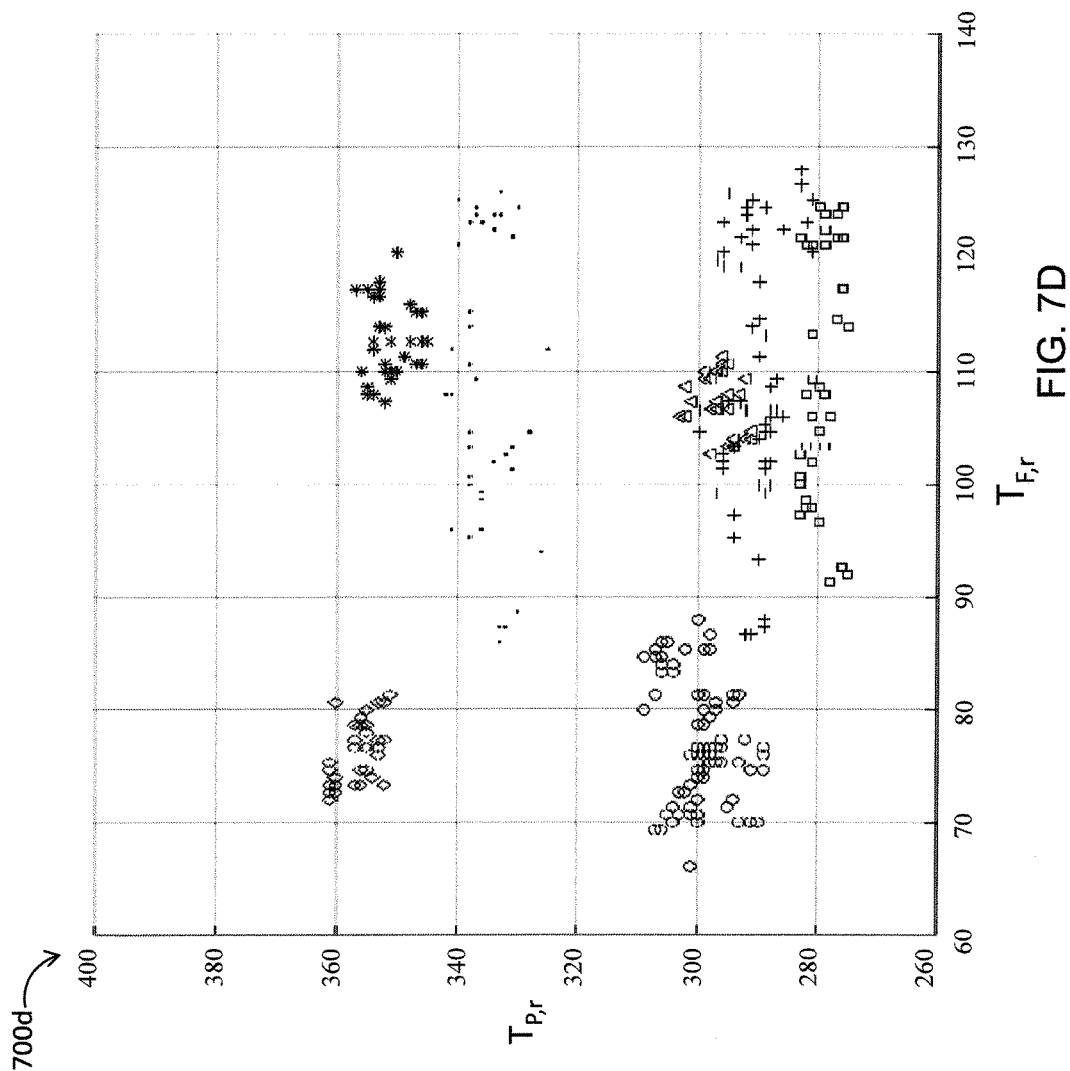

FIGS. 7B-7D show 2D projections of the 3D graph in FIG. 7A. In particular, the graph 700b in FIG. 7B shows data points illustrating the pairs (R, $T_{F,r}$), the graph 700c in FIG. 7C shows data points illustrating the pairs ($T_{P,r}$, R), and the graph 700d of FIG. 7D shows data points illustrating the pairs ($T_{F,r}$, $T_{P,r}$). In other words, the same experimental data (or same measurement signals 200) is used to create the graphs 700a-700d. However, in the graphs 700b-700d, only two parameters (out of the three parameters R, $T_{F,r}$ and $T_{p,r}$) are used for each experiment (or each measurement signal), whereas in graph 700a, each data point corresponding to a respective measurement signal 200 includes the three parameters R, $T_{F,r}$ and $T_{p,r}$.

Comparing the results in FIG. 7A to those in FIGS. 7B-7D, one can see that the clusters of data points associated with separate pipe types are more distinguishable (e.g., non-overlapping and/or spaced away from each other) in graph 700a than in graphs 700b-700d. In other words, the results in FIGS. 7A-7D suggest that using the three parameters R, $T_{F,r}$ and $T_{p,r}$ as classification parameters can lead to better classification of measurement signals based on respective pipe types and, therefore, more reliable pipe type identification than when using only two of the three parameters R, $T_{F,r}$ and $T_{p,r}$. Also, comparing the results of FIGS. 7B and 7C, one can see that $T_{p,r}$ does a better job in distinguishing between M-copper pipes and L-copper pipes than $T_{F,r}$. However, $T_{F,r}$ does a better job in distinguishing between pipes of different diameters than $T_{p,r}$.

Figure 8:
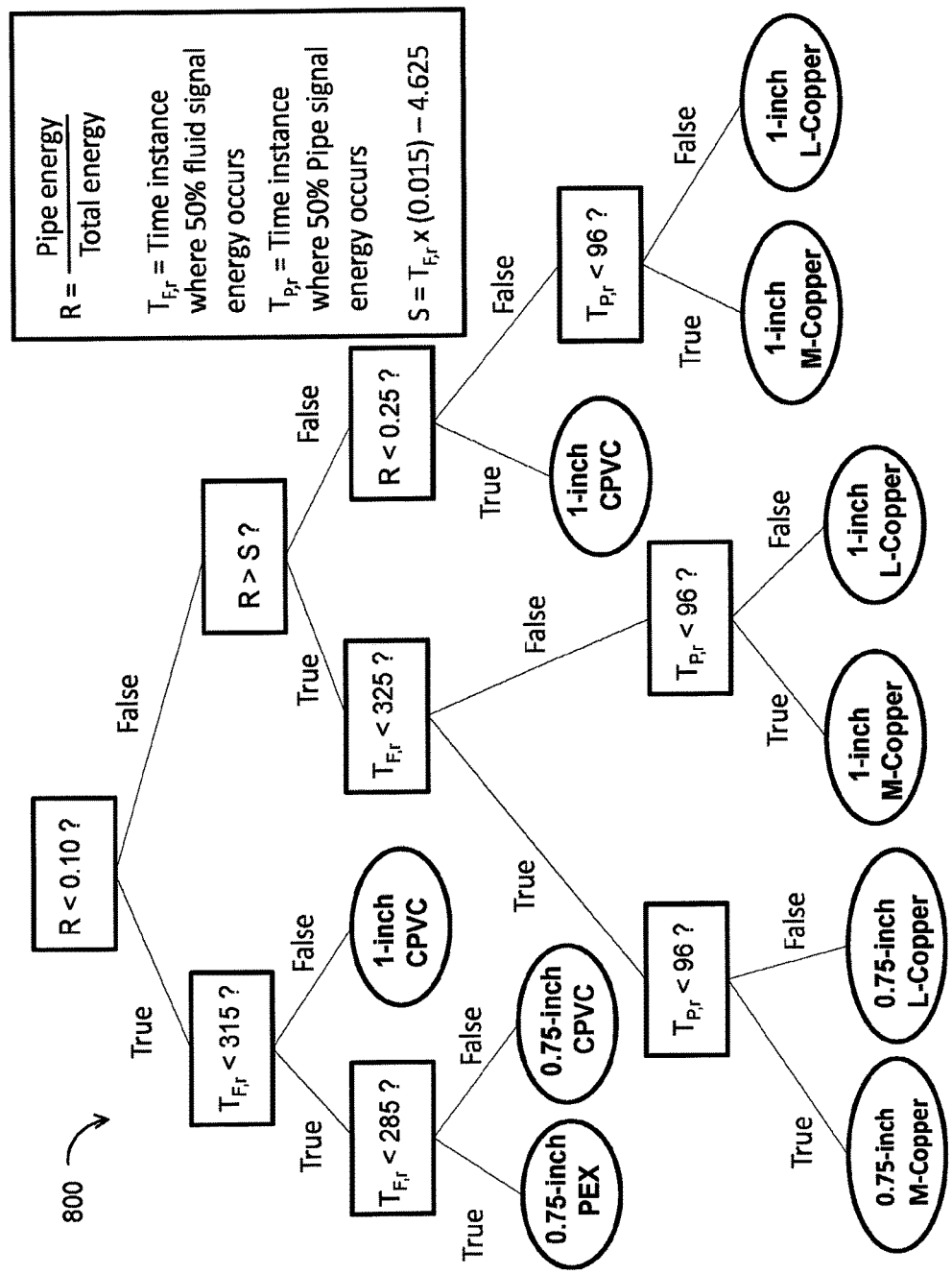
FIG. 8 shows a flow diagram illustrating a classification process based on the data clustering shown in FIG. 7A.

FIG. 8 shows a flow diagram illustrating a classification process 800 based on the data clustering shown in FIG. 7A. In the flow diagram, the values or mathematical expressions used in the decision boxes represent planes that separate between different clusters of data points. Such values or expressions can be computed, for example, based determining a mean data point for each cluster and using distances between the mean data points for different clusters. Other techniques known in the art can be used to identify planes (or lines in 2D) that best separate various clusters of data points.

The values or mathematical expressions for a classifier (such as the classification process 800 or the classification process 600) can be computed or determined using training or experimental data. The classifier (or classification process) can be implemented (using software, hardware or a combination thereof) in the fluid flow meter. For example, the values or mathematical expressions for a classifier can be stored in a memory of the fluid flow meter. The memory can store computer code instructions for executing the classifier (such as the classification process 600 or 800). When the fluid flow meter 100 is installed on a given pipe 10, the fluid flow meter 100 can generate one or more measurement signals (or receive signals). The generated receive signal(s) can include a downstream receive signal, an upstream receive signal, a zero-flow receive signal or a combination thereof. The controller 150 can execute the classifier (such as the classification process 600 or 800) to detect the pipe type of the pipe 10 on which the fluid flow meter 100 is mounted. In some embodiments, the classifier can be implemented on a remote computing device (such as a mobile device, a computer server, etc.) communicatively coupled to the fluid flow meter 100. The fluid flow meter 100 can generate one or more measurement (or receive signals) and transmit the measurement signals (or parameters thereof) to the remote device. The remote device can execute the classifier to identify the pipe type of the pipe 10 on which the fluid flow meter 100 is mounted based on the measurement signal(s) (or the parameters thereof). The remote device can then provide an indication of the pipe type to the fluid flow meter 100. Whether the pipe type is identified by the fluid flow meter or a remote device, the fluid flow meter can use the identified pipe type to select (or identify) one or pipe-type-dependent parameters (such as a lookup table or a proportionality constant between fluid flow rate and difference in propagation times between upstream and downstream signals) for use to estimate fluid flow rate (or fluid flow velocity).

While the examples provided above describe examples of detecting (or identifying) a pipe type among a plurality of pipe types, such examples are not limiting and are provided for illustrative purposes. For example, the methods and systems described herein are applicable to any number of pipe types. Also, other signal parameters or signal features, such as the energy values E, $E_F$ and/or $E_P$, time durations T, $T_F$, and/or $T_P$ of the measurement signal 200, the fluid measurement signal 201 and/or the pipe measurement signals, respectively, can be used to identify the pipe type. For instance, any combination of the signal parameters (or signal features) E, $E_F$, $E_P$, T, $T_F$, $T_P$, R, $T_{F,r}$ and $T_{p,r}$ can be used as measurement (or receive) signal features to identify the pipe type. In such instance, the classifier is defined based on such combination of parameters. In some embodiments, other signal features such as wavelet coefficients, signal envelope(s), energy function(s) over time (e.g., a function illustrating signal energy or normalized signal energy at any time instant of the signal), etc., can be used (e.g., constructing a respective classifier) to identify pipe types.

In some embodiments, a Gaussian Mixture Model (GMM) can be used for classification. Signal feature values for each pipe type can be assumed (or modeled) to follow the distribution of a mixture of k different Gaussian probability density functions (e.g., due to meter variations, etc.). For example, training data for n pipe types (such as, experimental data including a plurality of measurement signals 200, or parameter/feature values thereof, and an indication of a pipe type for each of the measurement signals) can be used to generate a GMM such that each pipe type is associated with one or more Gaussian distributions in the GMM. For each pipe type, the respective signal features are modeled into a separate Gaussian mixture (which may be a sum of weighted Gaussian probability density functions (pdf)). For each of the n pipe types, the parameters for the respective mixture of Gaussian distributions can be estimated using the Expectation-Maximization (EM) algorithm on the training data. For example, the mean and variance of each Gaussian pdf in a mixture and the weight of each Gaussian pdf in the mixture is determined by the EM algorithm. The GMM can be constructed based on samples of measurement signals 200 or based on signal feature (or signal parameter) values of the measurement (or receive) signals. The GMM can be constructed based on any combination of signal features (or signal parameters) described in this disclosure or known in the art (such as any combination of the signal features E, $E_F$, $E_P$, T, $T_F$, $T_P$, R, $T_{F,r}$ and $T_{p,r}$, signal wavelet coefficients, signal envelopes for any combination of the signals 200, 201 and 202, signal samples or subsets thereof, etc.).

The controller 150 (or a processor of a remote device) can use the GMM to identify a pipe type of a pipe 10 on which a fluid flow meter 100 is mounted based on one or more measurement signals 200 generated by the fluid flow meter 100 (or parameter/feature values of the measurement signal(s) 200). Given a set of feature/parameter values of one or more measurement signals 200, the controller 150 (or a processor of a remote device communicatively coupled to the fluid flow meter 100) can compute (or determine) the probability of the set of feature/parameter values belonging to any of the n different Gaussian mixture distributions defined by the GMM. The controller 150 (or a processor of a remote device communicatively coupled to the fluid flow meter 100) can choose the class (or pipe type) corresponding to the Gaussian mixture distribution with the highest probability.

Figure 9:
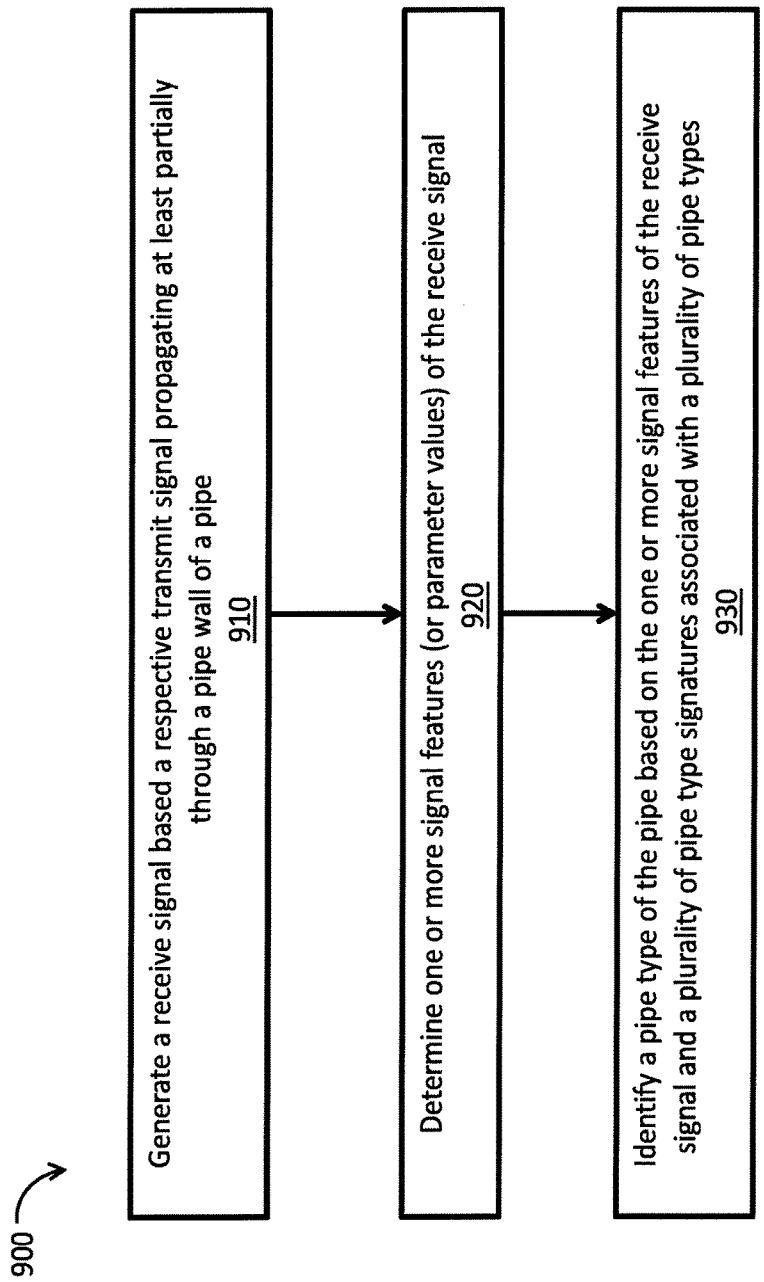
FIG. 9 shows a flow diagram depicting a method of identifying (or detecting) a pipe type based on a measurement (or receive) signal corresponding to a transmit signal.

FIG. 9 shows a flow diagram depicting a method 900 of identifying (or detecting) a pipe type based on a receive (or measurement) signal corresponding to a respective transmit signal. The method 900 can include generating a receive, or measurement, signal based a respective transmit signal propagating at least partially through a pipe wall of a pipe (step 910). The method 900 also can include determining (or computing) one or more signal features (or parameter values) of the receive signal (step 920). The method 900 also can include identifying a pipe type of the pipe based on the one or more signal features (or parameter values) of the receive signal and a plurality of pipe type signatures associated with a plurality of pipe types, for each pipe type of the plurality of pipe types, the respective pipe type signature includes one or more characteristics of receive (or measurement) signals associated with that pipe type (step 930).

The method 900 can include a sensor (such as an ultrasonic sensor) of a fluid flow meter generating a receive, or measurement, signal based a respective transmit signal propagating at least partially through a pipe wall of a pipe (step 910). For an ultrasonic sensor having two or more transducers, generating the receive signal can include a first transducer transmitting the transmit signal to propagate at least partially through a fluid flowing in the pipe, and a second transducer receiving a receive signal associated with the transmit signal. The receive signal represents a received version of the transmit signal. The receive signal can be a time-delayed and distorted version of the transmit signal. For instance, the receive signal can include a first signal portion that represents a received version of a respective first portion of the transmit signal propagating mainly on, or within, the pipe wall between the two transducers, and a second signal portion that represents a received version of a respective second portion of the transmit signal propagating mainly through the fluid between the two transducers. In other words, the first and the second portions of the transmit signal can be associated with two distinct propagation paths. Generating the receive signal can include sampling, e.g., by an ADC of the fluid flow meter, the receive signal.

The method 900 also can include determining (or computing) one or more signal features (or parameter values) of the receive signal (step 920). The controller 150 of the fluid flow meter 100 can use samples of the receive signal to determine or compute the signal feature(s) of the receive signal. Determining (or computing) the signal feature(s) can include the controller 150 (or a processor of a remote device communicatively coupled to the fluid flow meter 100) computing the value(s) for any combination of the signal parameters E, $E_F$, $E_P$, T, $T_F$, $T_P$, R, $T_{F,r}$ and $T_{p,r}$. Values of any of the parameters E, $E_F$, $E_P$, T, $T_F$, $T_P$, R, $T_{F,r}$ and $T_{p,r}$ can be computed as described above for each of these parameters. Determining (or computing) the signal feature(s) can include the controller 150 (or a processor of a remote device communicatively coupled to the fluid flow meter 100) computing signal wavelet coefficients of the receive signal, the first signal portion of the receive signal or the second signal potion of the receive signal. Determining (or computing) the signal feature(s) can include the controller 150 (or a processor of a remote device communicatively coupled to the fluid flow meter 100 ) computing signal envelope(s) of the receive signal (such as measurement signal 200), the first signal portion of the receive signal (such as the pipe measurement signal 202) or the second signal potion of the receive signal (such as the fluid measurement signal 201). Determining (or computing) the signal feature(s) can include the controller 150 (or a processor of a remote device communicatively coupled to the fluid flow meter 100) selecting one or more signal samples of the receive signal. For example, the controller 150 can select samples of the first signal portion of the receive signal (e.g., pipe measurement signal 202) that are greater than a first threshold and/or samples of the second signal portion of the receive signal (e.g., fluid measurement signal 201). Determining (or computing) the signal feature(s) can include the controller 150 (or a processor of a remote device communicatively coupled to the fluid flow meter 100) identifying the first signal portion of the receive signal (such as identifying the start and end times $k_{p,s}$ and $k_{p,e}$ of the first signal portion of the receive signal), and/or identifying the second signal portion of the receive signal (such as identifying the start and end times $k_{f,s}$ and $k_{f,e}$ of the second signal portion of the receive signal). As illustrated above, computing some of the signal features, such as the value of $T_{F,r}$ or $T_{p,r}$, can include using the start and end times of the first or second signal portions of the receive signal.

The method 900 can include identifying a pipe type of the pipe based on the one or more signal features (or parameter values) of the receive signal and a plurality of pipe type signatures associated with a plurality of pipe types (step 930). The fluid flow meter 100 can include a memory storing plurality of pipe type signatures associated with a plurality of pipe types. For each pipe type of the plurality of pipe types, the respective pipe type signature can include one or more characteristics of receive (or measurement) signals associated with that pipe type. For example, each signal pipe type signature can include one or more values, ranges, or regions of one or more signal parameters of receive signals, such as values, ranges, or regions of any combination of the signal parameters E, $E_F$, $E_P$, T, $T_F$, $T_P$, R, $T_{F,r}$ and $T_{p,r}$. As discussed above, for instance with regard to FIGS. 3, 5 and 7A, the values, ranges or regions can define boundaries of cluster (or classification) regions of the parameters for that pipe type. In some embodiments, for each pipe type, the respective pipe type signature can include statistical characteristics of one or more receive signal parameters. For example, a GMM includes statistical parameters (such as mean and variance) for each Gaussian distribution associated with any pipe type. Each Gaussian distribution represents a probabilistic distribution of one or more signal parameters.

Identifying the pipe type can include the controller 150 (or a processor of a remote device communicatively coupled to the fluid flow meter 100) using a classifier, such as a GMM classifier, a classification process similar to process 600 or 800, or any other classifier known in the art. The controller 150 (or a processor of a remote device communicatively coupled to the fluid flow meter 100) can use the one or more signal features (or signal parameter values) as input to the classifier. The classifier can be implemented as computer code instructions executable by the controller 150 (or a processor of a remote device communicatively coupled to the fluid flow meter 100).

In some embodiments, the controller 150 (or a processor of a remote device communicatively coupled to the fluid flow meter 100) can use multiple receive signals to identify the pipe type. The controller 150 (or a processor of a remote device communicatively coupled to the fluid flow meter 100) can determine (or compute) a set of signal features for each of the multiple receive signals. The controller 150 (or a processor of a remote device communicatively coupled to the fluid flow meter 100) can apply the signal features of the multiple receive signals either simultaneously or one set at a time to the classifier. The controller 150 (or a processor of a remote device communicatively coupled to the fluid flow meter 100) can use classification results associated with the multiple sets of signal features to determine a final pipe type. For example, the most frequent pipe type in the multiple results can be selected as the final pipe type identified by the controller 150 (or a processor of a remote device communicatively coupled to the fluid flow meter 100).

The controller 150 can select or adjust a calibration parameter value of the fluid flow meter 100 based on the pipe type identified. The calibration parameter value can be a parameter value used by the controller 150 in measuring or estimating fluid flow rate (or fluid flow velocity) based on one or more measurement signals. In some embodiments, a memory of the fluid flow meter can store a plurality of calibration parameter values associated with a plurality of pipe types. The controller can select a value from the plurality of calibration parameter values based on the pipe type identified.

The classifier (or the classification information) can be obtained through experimental data gathered using different types of pipes. The experimental data can include a plurality of receive signals associated with various pipes of different types. For example, signal energy and signal time parameters can be extracted from the receive signals and respective clusters associated with different pipe types can be identified. The classification information can include information identifying the different clusters.

While the invention has been particularly shown and described with reference to specific embodiments, it should be understood by those skilled in the art that various changes in form and detail may be made therein without departing from the spirit and scope of the invention as defined by the following claims. Also, the systems, devices and methods disclosed herein can be applied in water flow meters or in fluid flow meters for monitoring flow of other fluids (such as natural gas, gasoline or oil). The systems, devices, and methods disclosed herein can be applied to distinguish between any number of pipe types. The controller can include an ASIC-based system, such as a Maxim zero-crossing-based chip or a Microchip charge time measurement unit (CTMU) ASIC. The energy parameter value(s) can be computed based on a receive analog signal using, for instance, signal filtering, signal rectification, and signal integration over a configurable time window.

What is claimed is:

1. A fluid flow meter comprising:
    an ultrasonic sensor including a first ultrasonic transducer capable of transmitting a transmit signal to propagate, at least partially, through a fluid in a pipe and a second ultrasonic transducer capable of receiving a respective receive signal;
    a memory storing computer code instructions and a plurality of pipe type signatures associated with a plurality of pipe types, each pipe type signature of a respective pipe type of the plurality of pipe types including one or more characteristics of receive signals associated with that pipe type; and
    a processor, communicatively coupled to the sensor and to the memory, configured to, when executing the computer code instructions:
        compute, using the receive signal, a relative energy parameter indicative of a relative pipe signal energy of a pipe signal compared to a total energy of the receive signal, the pipe signal representing a first portion of the receive signal corresponding to a respective first portion of the transmit signal propagating substantially on, or within, a wall of the pipe between the first ultrasonic transducer and the second ultrasonic transducer, and the fluid signal representing a second portion of the receive signal corresponding to a respective second portion of the transmit signal propagating substantially through the fluid in the pipe between the first ultrasonic transducer and the second ultrasonic transducer;
        determine a time value indicative of a time instance at which a specific fraction of energy of the fluid signal is received at the second ultrasonic transducer; and
        identify, using the relative energy parameter, the time value, and a classifier defined based on the plurality of pipe type signatures, a pipe type of the pipe.

2. The fluid flow meter of claim 1, wherein the plurality of pipe type signatures include values, ranges, or regions associated with the relative energy parameter and the time value indicative of the time instance at which the specific fraction of energy of the fluid signal is received at the second ultrasonic transducer.

3. The fluid flow meter of claim 2, wherein identifying a pipe type of the pipe includes comparing the relative energy parameter and the time value to respective values, ranges or regions in the plurality of pipe type signatures.

4. The fluid flow meter of claim 1, wherein the classifier includes a Gaussian mixture model (GMM) classifier.

5. The fluid flow meter of claim 4, wherein identifying a pipe type of the pipe includes:
    computing, for each Gaussian mixture distribution defined by the GMM classifier, a probability of the relative energy parameter and the time value belonging to that Gaussian mixture distribution; and
    selecting the pipe type corresponding to the Gaussian mixture distribution associated with the highest probability.

6. The fluid flow meter of claim 1, wherein the processor is further configured, when executing the computer code instructions, to select or adjust a calibration parameter value of the fluid flow meter based on the identified pipe type.

7. The fluid flow meter of claim 1, wherein the processor is configured, when executing the computer code instructions, to filter the receive signal using a bandpass filter.

8. The fluid flow meter of claim 1, wherein the processor is a processor of the fluid flow meter or a processor of a computing device communicatively coupled to the fluid flow meter.

9. A method of identifying a pipe type of a pipe associated with a fluid flow meter comprising:

transmitting, by a first ultrasonic transducer of an ultrasonic sensor of the fluid flow meter, a transmit signal to propagate, at least partially, through a fluid in the pipe;

receiving, by a second ultrasonic transducer of the ultrasonic sensor, a receive signal responsive to transmitting the transmit signal;

storing, by a memory, a plurality of pipe type signatures associated with a plurality of pipe types, each pipe type signature of a respective pipe type of the plurality of pipe types including one or more characteristics of receive signals associated with that pipe type;

computing, by the processor using the receive signal, a relative energy parameter indicative of a relative pipe signal energy of a pipe signal compared to a total energy of the receive signal, the pipe signal representing a first portion of the receive signal corresponding to a respective first portion of the transmit signal propagating substantially on, or within, a wall of the pipe between the first ultrasonic transducer and the second ultrasonic transducer, and the fluid signal representing a second portion of the receive signal corresponding to a respective second portion of the transmit signal propagating substantially through the fluid in the pipe between the first ultrasonic transducer and the second ultrasonic transducer;

determining, by the processor using the receive signal, a time value indicative of a time instance at which a specific fraction of energy of the fluid signal is received at the second ultrasonic transducer; and identifying, by the processor, using the relative energy parameter, the time value, and a classifier defined based on the plurality of pipe type signatures, a pipe type of the pipe.

10. The method of claim 9, wherein the plurality of pipe type signatures include values, ranges, or regions associated with the relative energy parameter and the time value indicative of the time instance at which the specific fraction of energy of the fluid signal is received at the second ultrasonic transducer.

11. The method of claim 10, wherein identifying a pipe type of the pipe includes comparing the relative energy parameter and the time value to respective values, ranges or regions in the plurality of pipe type signatures.

12. The method of claim 9, wherein the classifier includes a Gaussian mixture model (GMM) classifier.

13. The method of claim 12, wherein identifying a pipe type of the pipe includes:
computing, for each Gaussian mixture distribution defined by the GMM classifier, a probability of the relative energy parameter and the time value belonging to that Gaussian mixture distribution; and
selecting the pipe type corresponding to the Gaussian mixture distribution associated with the highest probability.

14. The method of claim 9 further comprising selecting or adjusting a calibration parameter value of the fluid flow meter based on the identified pipe type.

15. The method of claim 9 further comprising filtering the receive signal using a bandpass filter.

16. A non-transitory computer-readable medium with computer code instructions stored thereon, the computer code instructions, when executed by a processor, cause the processor to:
cause a sensor of a fluid flow meter to transmit a transmit signal for propagating, at least partially, through a fluid in a pipe, and receive a receive signal responsive to transmitting the transmit signal;
compute, using the receive signal, a relative energy parameter indicative of a relative pipe signal energy of a pipe signal compared to a total energy of the receive signal, the pipe signal representing a first portion of the receive signal corresponding to a respective first portion of the transmit signal propagating substantially on, or within, a wall of the pipe between the first ultrasonic transducer and the second ultrasonic transducer, and the fluid signal representing a second portion of the receive signal corresponding to a respective second portion of the transmit signal propagating substantially through the fluid in the pipe between the first ultrasonic transducer and the second ultrasonic transducer;
determine a time value indicative of a time instance at which a specific fraction of energy of the fluid signal is received at the second ultrasonic transducer; and
identify, using the relative energy parameter, the time value, and a classifier defined based on a plurality of pipe type signatures, a pipe type of the pipe.

17. The non-transitory computer-readable medium of claim 16, wherein the plurality of pipe type signatures include values, ranges, or regions associated with the relative energy parameter and the time value indicative of the time instance at which the specific fraction of energy of the fluid signal is received at the second ultrasonic transducer.

18. The non-transitory computer-readable medium of claim 17, wherein identifying a pipe type of the pipe includes comparing the relative energy parameter and the time value to respective values, ranges or regions in the plurality of pipe type signatures.

19. The non-transitory computer-readable medium of claim 16, wherein the classifier includes a Gaussian mixture model (GMM) classifier and wherein identifying a pipe type of the pipe includes:
computing, for each Gaussian mixture distribution defined by the GMM classifier, a probability of the relative energy parameter and the time value belonging to that Gaussian mixture distribution; and
selecting the pipe type corresponding to the Gaussian mixture distribution associated with the highest probability.

20. The non-transitory computer-readable medium of claim 16, wherein the computer code instructions, when executed by the processor, further cause the processor to select or adjust a calibration parameter value of the fluid flow meter based on the identified pipe type.

* * * * *